United States Patent [19]
Kozak et al.

[11] Patent Number: 5,397,364
[45] Date of Patent: Mar. 14, 1995

[54] ANTERIOR INTERBODY FUSION DEVICE

[75] Inventors: Jeffrey Kozak, Houston, Tex.; Larry Boyd, Memphis, Tenn.

[73] Assignee: Danek Medical, Inc., Memphis, Tenn.

[21] Appl. No.: 134,049

[22] Filed: Oct. 12, 1993

[51] Int. Cl.6 .............................................. A61F 2/44
[52] U.S. Cl. ......................................... 623/17; 606/61
[58] Field of Search ............................. 623/17, 11, 16

[56] References Cited

U.S. PATENT DOCUMENTS

| | | | |
|---|---|---|---|
| 4,759,766 | 7/1988 | Buettner-Janx et al. | 623/17 |
| 4,772,287 | 9/1988 | Ray et al. | 623/17 |
| 4,863,476 | 9/1989 | Shepperd | 623/17 |
| 4,878,915 | 11/1989 | Brantigan | 623/17 |
| 4,892,545 | 1/1990 | Day et al. | 623/17 |
| 4,904,261 | 2/1990 | Dove et al. | 623/17 |
| 4,917,704 | 4/1990 | Frey et al. | 623/17 |
| 4,932,975 | 6/1990 | Main et al. | 623/17 |
| 4,936,848 | 6/1990 | Bagby | 623/17 |
| 5,002,576 | 3/1991 | Fuhrmann et al. | 623/17 |
| 5,147,404 | 9/1992 | Downey | 623/17 |
| 5,192,327 | 3/1993 | Brantigan | 623/17 |

FOREIGN PATENT DOCUMENTS

WO90/00037 1/1990 WIPO.
WO92/14423 9/1992 WIPO.

*Primary Examiner*—David Isabella
*Attorney, Agent, or Firm*—Woodard, Emhardt, Naughton, Moriarty & McNett

[57] ABSTRACT

An interbody fusion device includes a pair of lateral spacers and a pair of central spacers, each sized for percutaneous introduction through a disc resection portal in the disc annulus. Each of the lateral spacers includes opposing side faces defining a channel therein, while each of the central spacers includes arms at their opposite ends configured to be received within a channel of a corresponding lateral spacer. The arms and channels are interlocking to prevent separation of the components once assembled within the intradiscal space. The assembly of the central and lateral spacers defines a cavity therebetween for insertion of bone graft material. The central and lateral spacers are configured so that the bone graft cavity is oriented over the weakest, but most vascular and biologically active, bone of the vertebral body, while the lateral spacers are situated adjacent the disc annulus and over the strongest vertebral bone.

18 Claims, 9 Drawing Sheets

ANTERIOR INTERBODY FUSION DEVICE

BACKGROUND OF THE INVENTION

This invention relates to spinal implants for use as anterior fixation devices, and to an implant which is to be placed into the intervertebral space left after the removal of a damaged spinal disc to assist in promoting interbody fusion.

A major cause of persistent, often disabling, back pain can arise by disruption of the disc annulus, chronic inflammation of the disc, or relative instability of the vertebral bodies surrounding a given disc, such as might occur due to a degenerative disease. In the more severe, disabling cases, some form of mechanical limitation to the movement of vertebrae on either side of the subject disc is necessary. In the more severe cases, the disc tissue is irreparably damaged, thereby necessitating removal of the entire disc. However, when the disc nucleus is removed without subsequent stabilization, the same disabling back pain often recurs due to persistent inflammation and/or instability.

Various approaches have been developed to stabilize the adjacent vertebral bodies following excision of the disc material. In one approach, two adjacent vertebra are fused posterio-laterally, according to a standard technique, by rigid plates engaged at their ends to respective vertebrae by way of screws. However, it has been found that posterior fusion with rigid plates can be associated with pseudoarthrosis and implant loosening and/or failure.

Another approach involves the use of posterio-lateral fusion and rigid posterior instrumentation, as described above, with the addition of an interbody graft or implant placed from the posterior approach. Although a significant improvement in fusion rate can be achieved with this approach, scarring of the spinal nerves can occur which may lead to pain or neurologic deficit.

In yet another approach, anterior grafts are implemented. Three general types of anterior devices are presently known. In one type, the entire vertebral body is replaced by an implant that spans the vertebral and two surrounding intradiscal spaces. This approach is frequently used where the vertebral body is also damaged by way of a tumor, a fracture and the like. In another approach, only the disc is replaced by a prosthetic disc. In this approach, the object is not fusion between the vertebrae at the instrumented level, but rather replacement of the disc mechanical features by an implant.

A third approach, to which the present invention is more particularly directed, concerns a device adapted to promote fusion or arthrodesis across the intradiscal space. In the upper lumbar spine, bone grafts can be placed within the disc and the surrounding vertebrae can be stabilized with a plate placed on the lateral vertebral body using screws projecting into the bodies. This approach is not possible in the lower lumbar disc spaces due to the regional vascular anatomy. Unfortunately, more than 90% of the lumbar fusions are performed in the lower lumbar region. Therefore, there exists a need for a device to stabilize adjacent vertebrae, such as in the lower lumbar region, which device is primarily confined within the given disc space.

While a few devices of this type are known (such as the device of Dove shown in U.S. Pat. No. 4,904,261), there remains a need for an anterior lumbar interbody fusion device that will improve the fusion rate between the adjacent vertebrae, while also preventing disc interspace collapse due to end plate cavitation, for instance. There is also a need for a fusion device that is safe and effective and still consistent with traditional surgical arthrodesis practice.

In connection with the development of the interbody, fusion device of the present invention, Applicants have ascertained certain design principals that should be met for a safe and effective device. One important principal is that the load transmitted between adjacent vertebrae should be on the strongest part of the vertebral body. One problem with some prior art fusion devices, and even some prosthetic disc devices, is that a large portion of the load is reacted against the weakest part of the vertebral body which can lead to cavitation of the device into the surrounding vertebral endplates with subsequent collapse of the intradiscal space and even damage to the vertebra itself.

Further, a preferred interbody fusion device should fit the patient's intradiscal anatomy and restore, as close as possible, the proper anatomic relationship of the disc, pedicle, nerve root and facet joint in order to avoid future physiological problems. Restoration of the normal disc height will also return the disc annulus to tension, reducing annular bulge or prolapse and promoting interspace stability. At the same time, the device should not shield the lumbar spine from all of the stresses normally borne by the spine, since it has been found that reduction of normal stress on the vertebrae can result in loss of bone mass and strength.

Finally, the interbody fusion device should provide enough interspace rigidity to eliminate the need for external fixation or rigid fixation plates. With these goals in mind, Applicants have developed the anterior interbody fusion device and method of the present invention.

SUMMARY OF THE INVENTION

The present invention contemplates an interbody fusion device configured for insertion into the intradiscal space following resection of the disc material through a portal in the disc annulus. The device includes a pair of lateral spacers formed in a generally semicircular configuration and occupying less than half of the area of the intradiscal space. Each of the lateral spacers defines a channel in opposing and interiorly facing side faces. The device further includes a pair of central spacers, each configured at their respective ends for engaging the channels in the lateral spacers. The channels and ends of the central spacers are configured for interlocking engagement, such as a dovetail, so that the central spacers can be slidably inserted and removed only along the length of the channel. In other words, the interlocking feature between the lateral and central spacers maintains a predetermined and fixed lateral separation between the lateral spacers so that the lateral spacers are disposed adjacent the disc annulus and, more significantly, over the region of the vertebral body having the highest strength and load bearing capability.

Each component of the interbody fusion device, the lateral and central spacers, is sized for insertion through a single portal in the disc annulus. However, when assembled within the intradiscal space, the fusion device occupies the entire space, leaving only a central cavity between the spacers for the insertion of the bone graft material. This central cavity is situated over the weakest, but most vascular and biologically active, bone of the vertebral body. Clamping means, such as screws, are used to maintain the spacers in their assembled configuration within the intradiscal space.

The lateral spacers are provided with threaded bores in their anterior faces to receive the clamping screws. In addition, the bores accept an insertion rod that is used to guide the lateral spacers into the intradiscal space, and that is eventually used to spread the lateral spacers apart within the space. Once separated, the central spacers are inserted using a guide rod engaging a guide bore in each spacer. In this manner, the lateral and central spacers are assembled and interlocked like the pieces of a three-dimensional puzzle. Bone graft material is preferably inserted after the posterior central spacer has been positioned and before insertion of the anterior central spacer.

Alternative embodiments of the invention contemplate a fusion device having only one central spacer, and a device that accepts a number of bone screws to anchor the device to an adjacent vertebra. The invention further contemplates instruments for the insertion and assembly of the device components. In one particular aspect, rack and pinion driven spreader bars are used to spread the lateral spacers within the intradiscal space.

One important object of the present invention is to provide a fusion device that can restore or maintain the normal geometry of the intradiscal space, such as disc height and sagittal angle. Another object resides in the multiple component aspect of the device that permits the introduction of components that by themselves can be inserted through a typical disc resection portal, but when assembled within the intradiscal space occupy substantially the entire space.

A further object is to provide a device that is self-stabilizing within the disc space by providing convex surfaces to engage the concave vertebral body endplates.

Yet another object of the fusion device of the present invention is realized in that the multiple component aspect of the device permits the creation of a bone graft cavity at the most biologically and vascularly active area of the vertebral body, thereby encouraging strong and rapid fusion. Furthermore, the load bearing components of the device are situated over the strongest bone of the vertebrae.

Other objects, as well as certain benefits, achieved by the present invention will be readily discerned on consideration of the following written description and accompanying figures directed to the invention.

DESCRIPTION OF THE PREFERRED EMBODIMENTS

For the purpose of promoting an understanding of the principles of the invention, reference will now be made to the embodiments illustrated in the drawings and specific language will be used to describe the same. It will nevertheless be understood that no limitation of the scope or the invention is thereby intended, such alterations and further modifications in the illustrated device, and such further applications of the principles of the invention as illustrated therein being contemplated as would normally occur to one skilled in the art to which the invention relates.

Figure 1:
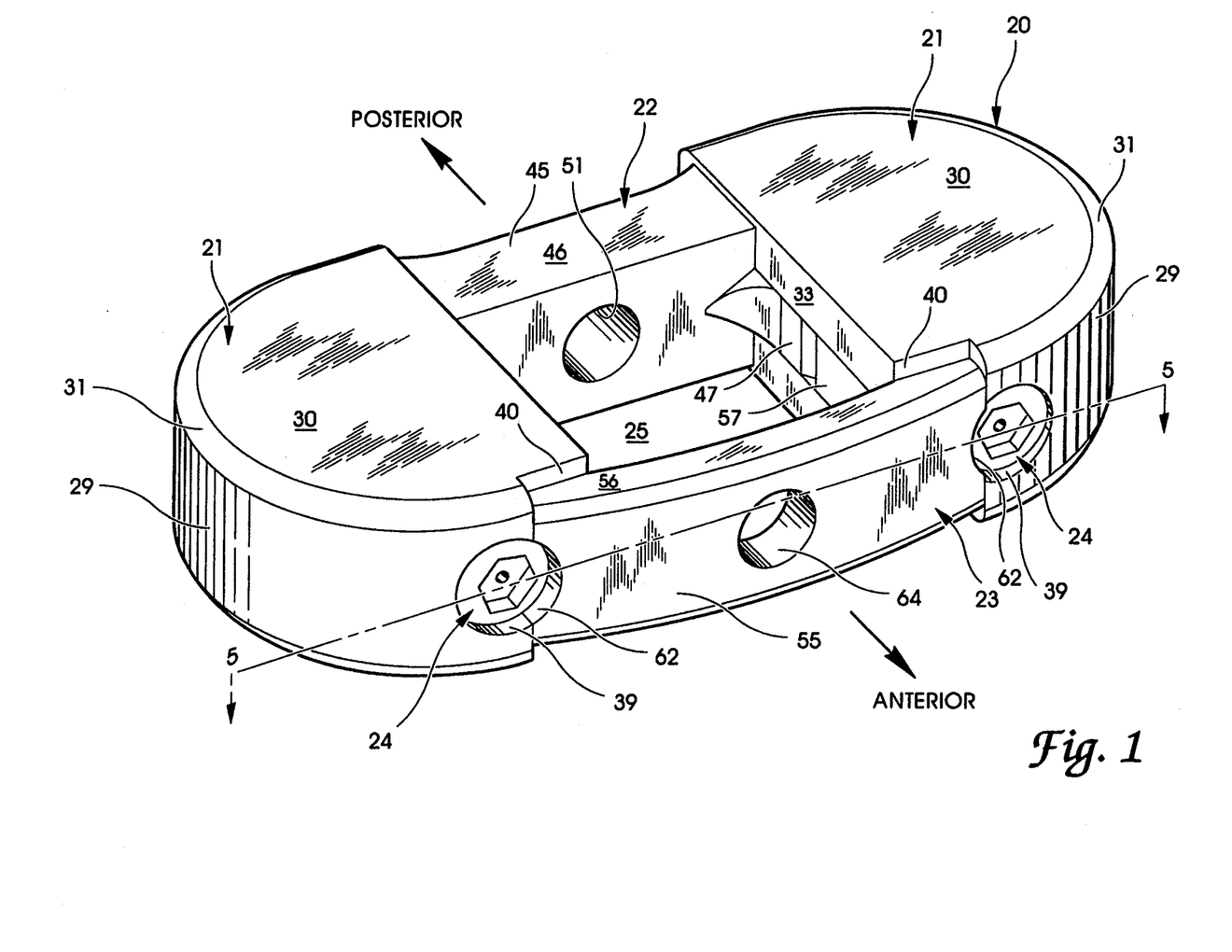
FIG. 1 is a top perspective view of a preferred embodiment of the anterior interbody fusion device of the present invention.

In accordance with one embodiment of the invention, an interbody fusion device 20 is depicted in FIG. 1. Generally, the fusion device 20 is a four component device. The device 20 includes a pair of lateral spacers 21, a posterior central spacer 22 and an anterior central spacer 23, the central spacers of which are engaged to the lateral spacers to hold them apart. A pair of fixation screws 24 are provided for locking the entire assembly together to form the completed fusion device 20. The fully assembled device 20 defines a cavity 25 between the lateral and central spacers, which cavity is adapted to receive bone graft material therein.

Figure 2:
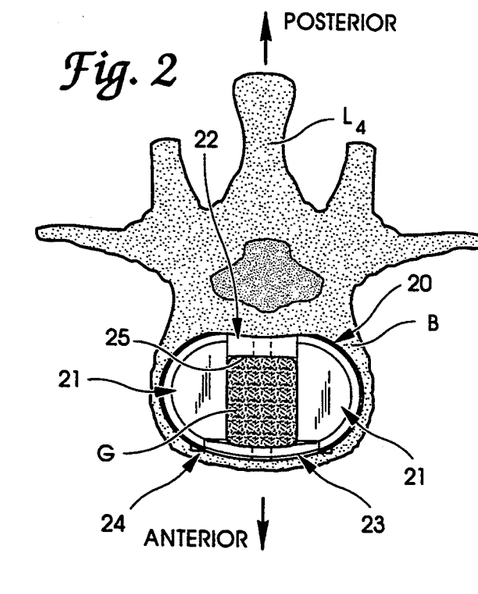
FIG. 2 is a top view of a lumbar vertebra with the interbody fusion device of FIG. 1 in position on the vertebral body.
Figure 3:
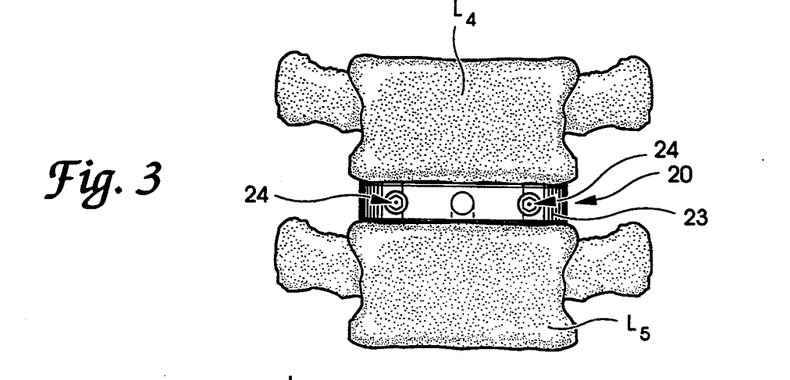
FIG. 3 is an A-P view of the interbody fusion device shown in FIG. 1 as disposed between two lumbar vertebrae.
Figure 4:
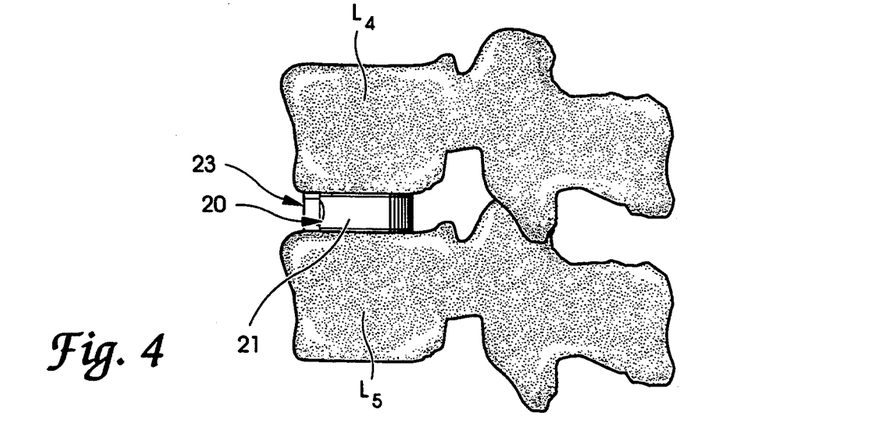
FIG. 4 is a view in the sagittal plane of the interbody fusion device oriented between adjacent vertebrae.

For example, the device 20 is shown situated between adjacent lumbar vertebrae $L_4$ and $L_5$ in FIGS. 2–4. More specifically, in FIG. 2, the device 20 is shown oriented against the vertebral body B. The cavity 25 defined by the components of the device 20 is filled with a bone graft material G. The graft material G could be cancellous bone or bone chips as is known in the art, or a suitable bone graft substitute material. As shown in FIGS. 3 and 4, the interbody fusion device 20 maintains the adjacent vertebrae L at the appropriate intradiscal distance. The bone graft material G fills the entire cavity 25 between the adjacent vertebrae, and over time fuses the two vertebrae together.

Figure 2A:
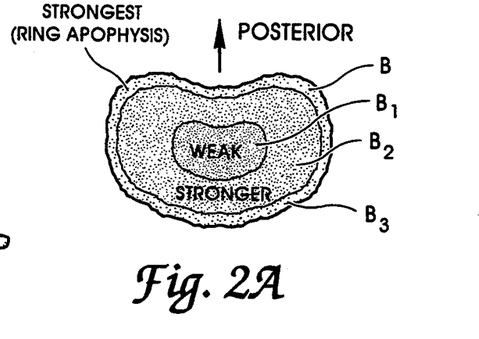
FIG. 2A is a representation of the vertebral body showing the regions of varying bone strength in the body.

A comparison between FIGS. 2 and 2A can illustrate one important feature of the present invention. In FIG. 2A, the vertebral body B is represented by its regions of bone strength. It has been discovered that the central kidney-shaped portion $B_1$ of the vertebral body B comprises mostly the weak cancellous bone. An annular kidney-shaped region $B_2$ around the central portion contains stronger bone, while the ring apophysis $B_3$ has the strongest bone of the vertebral body. With this in mind, the present invention strives to load those regions of the vertebral body B that have the strongest load-bearing capability. For example, the entire fusion device 20 assumes a generally annular kidney-shape, corresponding to the annular kidney-shape of the stronger bone $B_2$ and $B_3$ in the vertebral body B. This overall shape of the device 20 is achieved by the lateral spacers 21 having each a partial lens shape, while the posterior spacer 22 and anterior spacer 23 have an exterior contour generally corresponding to the central portions of the stronger vertebral body bone. The bone graft material G in the cavity 25 is generally positioned over the weakest portion $B_1$ of the vertebral body B. However, this portion $B_1$ is also known to be highly vascular and biologically active, so that it is an excellent location for bone graft incorporation and fusion.

Figure 5:
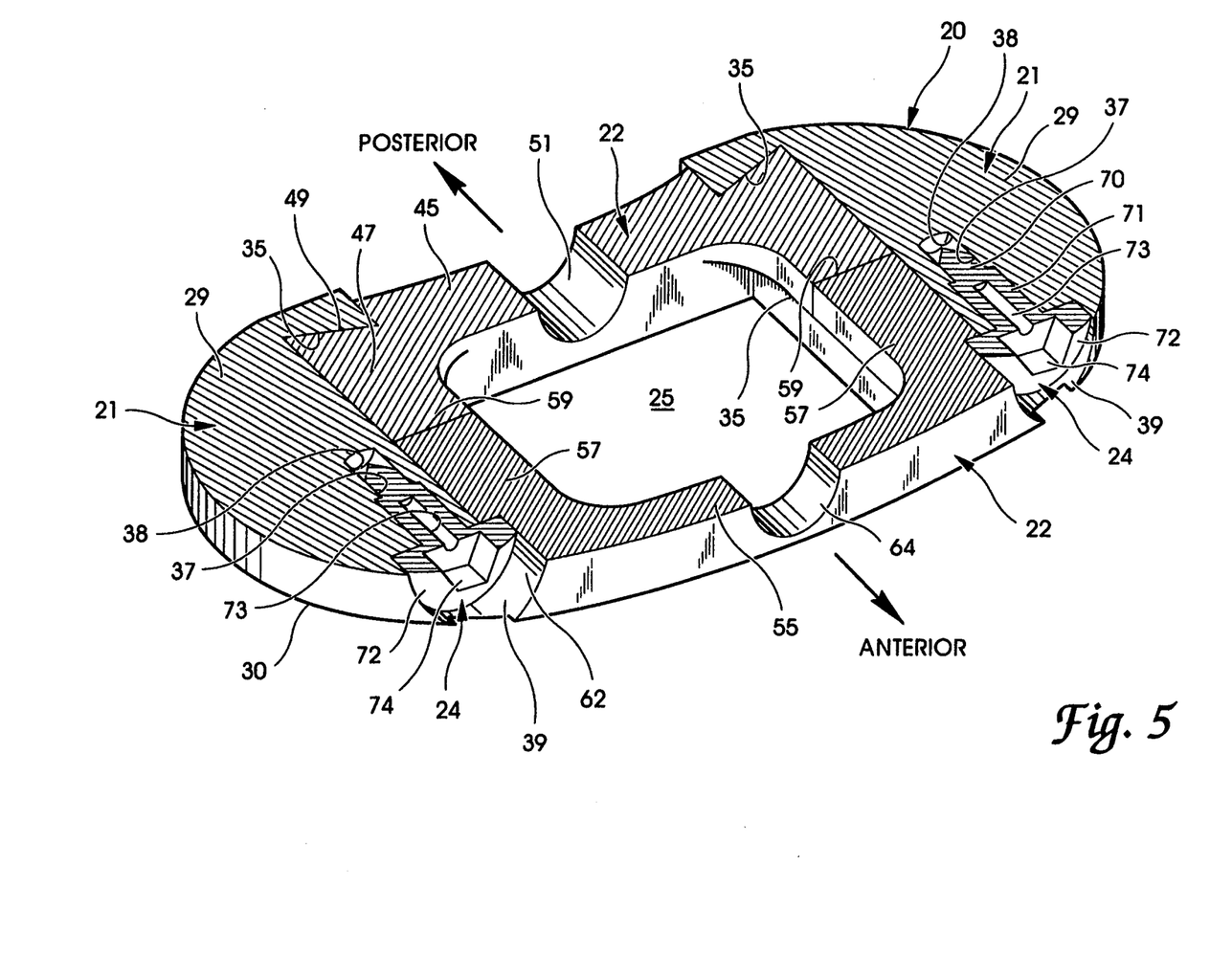
FIG. 5 is a top perspective cross-sectional view of the inter body fusion device shown in FIG. 1 taken along line 5—5 as viewed in the direction of the arrows.

Further details of the interbody fusion device 20 are shown in the cross-sectional view of the FIG. 5. In accordance with the present invention, the components are interlocking to increase the strength and rigidity of the assembled device 20, while implementing a construction that is easy to assemble to the close confines of a spinal surgical procedure. One problem with prior art devices that consist of but a single piece is that these devices are not readily adapted for modern anterior fusion techniques. In the early history of anterior fusion, a 15 inch incision was made through the abdomen and the relatively large single piece fusion components were implanted through that incision. Now, anterior fusion in preferably accomplished through a much smaller 1.5–2 inch incision without splitting any of the abdominal muscles. In a typical procedure, the surgeon will make an incision of this size to permit visualization of approximately 45° of the disc annulus. Newer disc resection techniques are readily adapted to incisions of this limited size. However, until Applicants' invention, no interbody fusion device was known by Applicants which provided load-sharing over such a significant portion of the vertebral body, yet which is still capable of being inserted through the small discectomy incisions.

Figure 6:
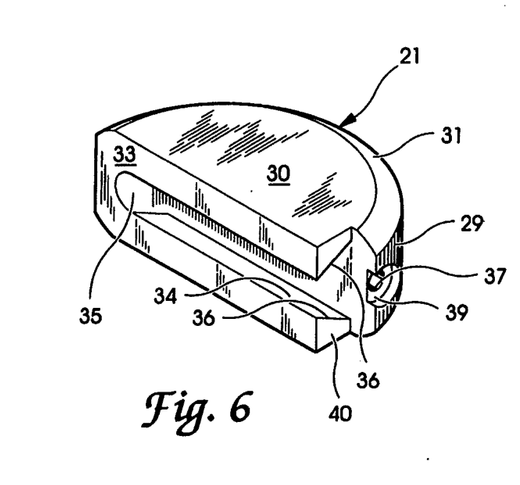
FIG. 6 is a top perspective view of a lateral spacer component of the fusion device shown in FIG. 1.

Thus, the interlocking components of the fusion device 20 have been configured for ease of insertion and ease of assembly. As can be seen in FIGS. 1 and 5–6, each lateral spacer 21 is fanned by a body 29 having opposite end plate faces 30. These end place faces 30 are configured to contact the end plates of the adjacent vertebral bodies. Preferably, the area of each of the end plate surfaces 30 is approximately $\frac{1}{8}$ of the total area occupied by the complete fusion device 20.

In a specific embodiment, the end plate faces 30 can include a porous biocompatible coating. In one specific embodiment, the lateral spacers 21, as well as the other components of the device, may be composed of titanium coated with a hydroxapatite coating. This coating can promote fusion between each of the lateral spacers 21 and the corresponding vertebral bodies B. Each of the end plate faces 30 includes a beveled edge 31 around the perimeter of the lateral spacer 21. The beveled edge 31 facilitates insertion between adjacent vertebrae and serves the obvious function of reducing trauma to surrounding tissue that might follow a device having sharp edges.

Figures 7, 11:
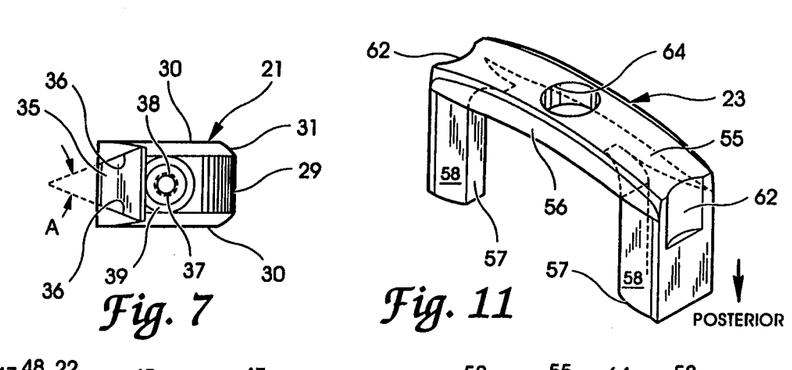
FIG. 7 is an end view of the lateral spacer component shown in FIG. 6.
FIG. 11 is a bottom perspective view of the anterior spacer component of the fusion device shown in FIG. 1.
Figure 8:
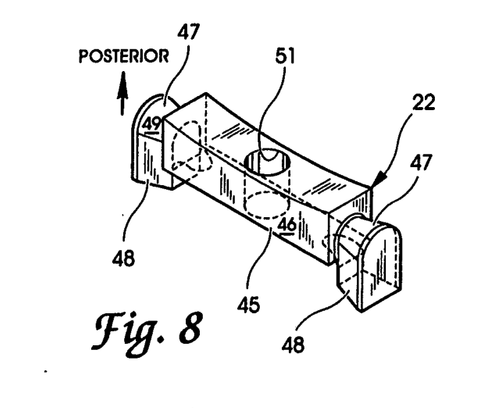
FIG. 8 is a bottom perspective view of the posterior spacer component of the fusion device shown in FIG. 1.
Figure 9:
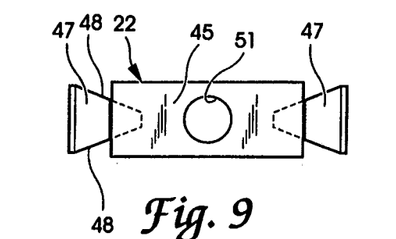
FIG. 9 is an end view of the posterior spacer component shown in FIG. 8.
Figure 10:
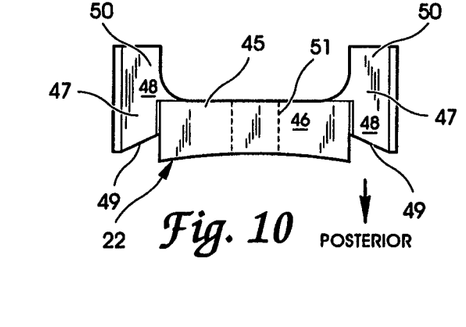
FIG. 10 is a top view of the posterior spacer component shown in FIG. 8.
Figures 12, 13:
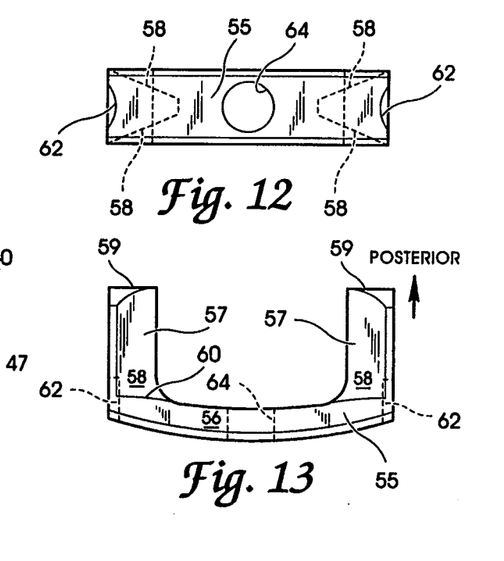
FIG. 12 is an end view of the anterior spacer component shown in FIG. 8.
FIG. 13 is a top view of the anterior spacer component shown in FIG. 8.

The body 29 of the lateral spacer 21 includes an interlock channel 24 defined in one side face 33 of the body, as shown most clearly in FIG. 6. The interlocking channel 34 has an end face 35 that is angled from the posterior to the anterior end of the device 20. The interlock channel 34 further includes opposite beveled walls 36 which are angled toward each other from the closed end to the open end of the channel, as readily seen in FIG. 7. These walls 36 are oriented to include an angle A, which in one specific embodiment is 45°.

The body 29 of each lateral spacer 21 further includes a screw bore 37 defined in the anterior face of the body 29. This screw bore 37 terminates at its base in a threaded bore 38 which is adapted to engage one of the fixation screws 24 shown in FIG. 1. The screw bore 37 also includes a head recess 39 which permits the head of the fixation screw to reside enshrouded within the body 20. The anterior face of each of the lateral spacers 29 also includes a spacer notch 40 defined in the body at the end of the interlock channel 34 and immediately adjacent the screw bore 37, as shown most clearly in FIG. 6.

The particular features of each lateral spacer 21 are adapted for interlocking engagement with each of the central spacers 22 and 23. First, describing the posterior central spacer 22, it can be seen in FIGS. 5 and 8–10, that the posterior spacer 22 includes a spacer body 45 having a pair of dovetail arms 47 projecting from the sides of the body. The dovetail arms 47 include opposite angled faces 48 which are configured to be engaged within the interlock channel 34 of each of the lateral spacers 21. Thus, each of the angled faces 48 defines an included angle approximately equal to the angle A at which the beveled walls 36 of the channel 34 are oriented.

Each of the dovetail arms 47 includes a curved end face 49 which is configured to mate with the curved end wall 35 of the interlock channel 34 in each lateral spacer 21. It can be seen from FIGS. 5 and 10 that the end face 49 of the dovetail arms 47 are also angled complimentary with the angle of the end wall 35 in the lateral spacers 21. Each of the dovetail arms 47 further includes an interior extension 50 to fill nearly half of the length of the interlock channel 34 in the lateral spacers bodies 29. Finally, the posterior spacer body 45 defined a central guide bore 51 therein which is used during assembly of the device, as will be described in more detail herein.

It can be seen, particularly from FIG. 5, that the posterior central spacer 22 is positioned with each of the dovetail arms 47 oriented into a respective interlock channel 34 in each of the lateral spacers 21. The posterior spacer 22 is moved along each of the channels until the end face 49 of each of the dovetail arms 47 contacts the end wall 35 of each of the interlock channels 34. The complimentary angular portions of the interlock channels 34 and the dovetails arms 47 prevent lateral separation between the components. That is, the posterior spacer body 22 maintains the lateral distance between each of the lateral spacers 21 when the interbody fusion device 20 is oriented between adjacent vertebrae.

A further component of the fusion device 20 is the anterior central spacer 23, which is shown in detail in FIGS. 4 and 11-13. In particular, the anterior central spacer 23 includes a spacer body 55 having a pair of posteriorly directed arms 57 extending therefrom. Each of the arms 57 includes opposite angled faced 58 which, like the dovetail arms 47 of the posterior spacer, are configured to engage within the interlock channels 34 in the lateral spacers 21. Each of the posterior arms 57 includes an end face 59 which directly abuts the end of each of the anterior extensions 50 of the dovetail arms 47 for the posterior central spacer 22. Thus, when both anterior and posterior spacers are engaged within the lateral spacer interlock channels 34, the two central spacers are firmly pressed into contact with each other.

The anterior spacer body 55 also includes an inner posteriorly directed face 60 adjacent each of the arms 57. This face 60 contacts a portion of the spacer notches 40 in each of the lateral spacers 21, in order to maintain the anterior spacer in position. The anterior spacer body 55 further includes a pair of notches 62 defined in the sides of the body and oriented along the anterior portion of the posterior directed arms 57. In the assembled configuration, these notches 62 align with the corresponding head recesses 39 in the lateral spacer bodies 29. The notches 62 in the anterior central spacer 23 combine with the head recesses 39 to form a generally circular recess to receive the head of a fixation screw 24 therein. Finally, the anterior spacer body 55 includes a central bore 64, which is aligned with the bore 51 in the posterior central spacer 22 when the device is being assembled.

As previously indicated, the interbody fusion device 20 of the present invention includes several components, each of which is small enough to be implanted through a typical anterior disc resection portal. More particularly, the area of each of the end faces of the components is substantially less than the area of the intradiscal space or annular region. For example, the area of the endplate face 30 of each of the lateral spacers 21 is less than half of the annular area. The end faces 46 of the posterior central spacer 22 and the end faces 56 of the anterior central spacer 23 occupy an area that is significantly less than the annular area (see, for example, FIG. 2). This minimal surface area and size of each of the components making up the interbody fusion device 20 means that the device can be used in minimally invasive procedures.

Thus, in one method of implanting the device, a standard anterior discectomy and distraction is performed. After the disc nucleus has been removed, the vertebral end plates can be prepared in a known fashion. Once the end plates of the adjacent vertebrae have been prepared, a pair of lateral spacers 21 can be inserted into the surgical site, with the adjacent vertebrae being separately distracted to permit proper location of each of the lateral spacers 21.

Figure 14:
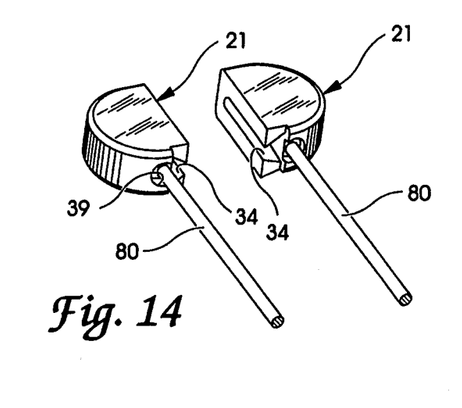
FIG. 14 is a top perspective view showing the placement of the lateral spacer components of the interbody fusion device shown in FIG. 1, as representative of a step in the method of implanting the device.
Figure 15:
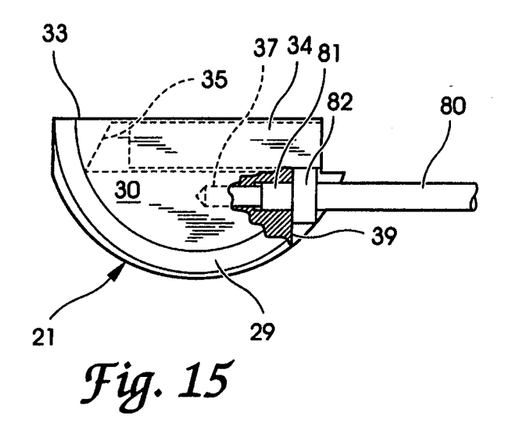
FIG. 15 is a top partial cross-sectional view showing a lateral spacer component of the interbody fusion device depicted in FIG. 14 with a spreader rod positioned in the device.
Figure 16:
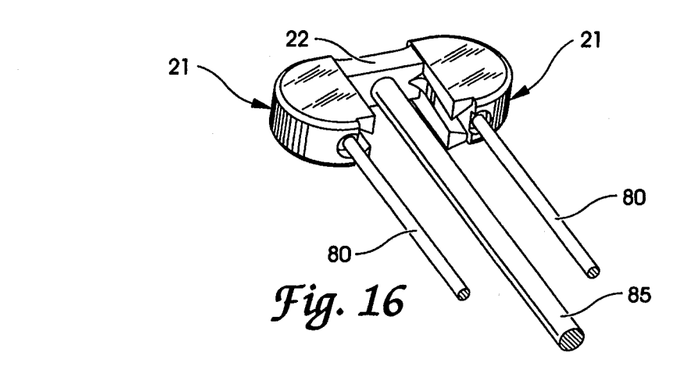
FIGS. 16–18 are top perspective views showing further steps of the insertion and assembly of the interbody fusion device.
Figure 17:
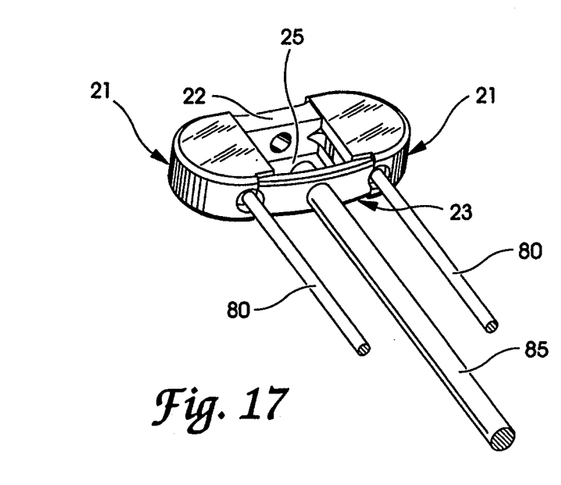

In one embodiment, introduction of each lateral spacer 21 is accomplished by way of a spreader rod 80, shown in FIG. 14. The details of the spreader rod 80 can be discerned from FIG. 15. In particular, it is seen that the spreader rod 80 includes a locator pin 81, which extends into the screw bore 37 of the lateral spacer body 29. The spreader rod 80 can also include a pusher stop 82 which has a diameter larger than the threaded bore but which is adapted to fit within the head recess 39 of the lateral spacer 21. The spreader rod 80 can then be used to manipulate and push the lateral spacers 21 into a proper position between the adjacent vertebrae. Preferably, the two lateral spacers 21 are initially inserted immediately side by side and even with their respective side faces 33 in direct contact. Once the spacers are generally arranged overlapping the vertebral body, the spacers 21 are separated by moving the spreader rods 80 apart using a separate spreader bar (not shown). The spreader bar can be configured to graft the ends of each of the spreader rods 80 external to the patient to push the bars apart, and thereby separate the lateral spacers 21 by an appropriate dimension.

Once the lateral spacers 21 are properly oriented, the posterior central spacer 22 is introduced into the patient. A guide rod 85 is provided for advancing the posterior central spacer 22 into proper position. In One specific embodiment, the guide rod 85 can be threaded to engage similar threads in the guide bore 51 of the posterior spacer 22. The spacer body is supported at the end of the guide rod 85, which is then used to advance and manipulate the posterior central spacer into position with its dovetail arms 47 oriented within the interlocking channels 34 of each of the lateral spacers 21. Some manipulation of the posterior central spacer 22 is generally required to position the dovetail arms 47 properly within each of the interlock channels 34. Thus, it is of some benefit to utilize a guide rod 85 that has some capability for gripping or engaging the central spacer.

Once the posterior spacer 22 is in position, the guide rod 85 can be unscrewed from the guide bore 51 of the posterior body 45 and removed from the patient. The guide rod 85 can then be threaded into the similarly threaded bore 64 in the anterior spacer 23, to facilitate introduction of the anterior central spacer 23. In one alternative, the guide rod 85 can be maintained in position in connection with the guide bore 51 of the posterior spacer body 45 and the anterior central spacer 22 advanced separately along the guide rod 85 into its proper position. A separate pusher would be required to gradually push the anterior spacer body 55 along the rod until it is oriented in its proper interlocking position. In this instance, the bore 64 in the anterior central spacer 23 would be unthreaded and be larger than the rod 85.

Prior to locating the anterior central spacer 23, the bone graft or bone graft substitute can be introduced into the cavity 25, which at that time is defined simply by the two lateral spacers 21 and the posterior spacer 22. Sufficient graft material should be introduced to completely fill the cavity 25, but still permit introduction of the anterior central spacer 23 to complete the device 20. Alternatively, the entire device can be assembled and the bone graft material introduced between the device and an adjacent vertebrae while the vertebrae are distracted. Yet another option is to complete the assembly and insert the bone graft G through the bore 64 in the anterior spacer 23.

Figure 18:
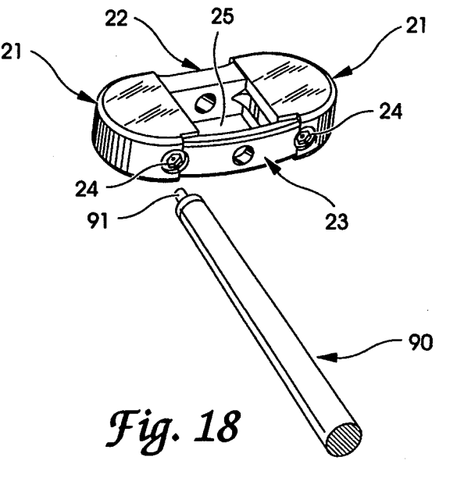
Figure 19:
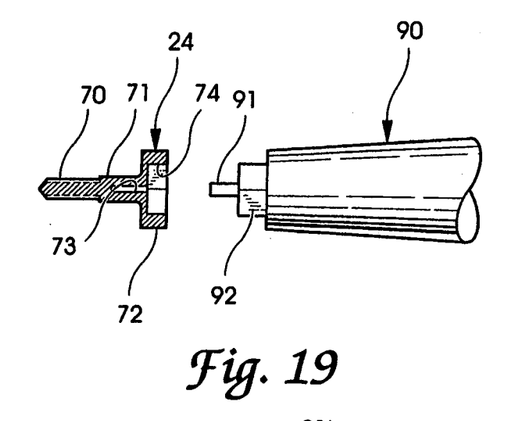
FIG. 19 is a top elevational partial cross-sectional view of the fixation screw used to couple the components of the device, along with the driving tool used to insert the screw.

Once the interlocking components of the fusion device 20 are in position between the adjacent vertebrae, the guide rod 85 and the spreader rods 80 can be removed. The entire assembly is clamped together by way of the fixation screws 24. As shown in FIGS. 5 and 19, each of the fixation screws includes a screw threaded portion 70 adapted to engage the threaded bore 38 of each of the lateral spacers 21. These screws also include a guide portion 71 which guides the screw into the screw bores 37. The head 72 of each screw is sized to be received within the head recess 39 in the lateral spacers 21. Each of the screws 24 includes a pin bore 73 extending into the screw from the head 72. Concentric with the pin bore is a driving tool recess 74, which in one specific embodiment, is a hex shaped recess. The pin bore 73 and driving tool recess 74 are configured to be engaged by a driving tool 90, which is used to insert the fixation screws 24, as shown in FIGS. 18 and 19.

The driving tool 90 includes a locator pin 91 which is adapted to be inserted into the pin bore 83. The pin 91 can be slightly bent so it "holds" the screw 24 on the tool when the pin extends into the bore 73. The tool 90 also includes a driving head 92 which in this specific embodiment is a hex head to be received within the driving tool recess 74. The driving tool 90 is thus used to guide each of the fixation screws 24 into the screw bores 37 and to tighten the screws into the bore to completely clamp each of the components of the device together.

The anterior interbody fusion device 20 of the present invention is a multi-component device adapted for insertion through the standard anterior disc resection portal. The device 20 is a static device, which means that the interdiscal spacing does not change with motion of the spine. It is therefore important that the dimensions of the device be proper when inserted in order to maintain the correct anatomical relationship of the patient's spine. It is thus contemplated that each of the lateral spacers 11 can be offered in a number of sizes to account for the intradiscal dimension, as well as the annular kidney-shaped region of stronger bone in the vertebral body at each level of the lumbar spine.

In one specific embodiment, each lateral spacer has a length of somewhat over 1 inch (25 mm) in the A-P direction and is formed at an outer radius of about 0.556 inches (14 mm), so that the lateral width of the spacer is about 0.588 inches (15 mm). In this same specific embodiment, the lateral spacer 20 is about 0.344 inches (8.5 mm) thick to correlate to the thickness of the patient intradiscal space. The lateral separation of each of the lateral spacers 21 is maintained by the posterior and anterior central spacers 22 and 23. Each of these spacers has a width between its interlocking arms of about 0.787 inches (20 mm) in the specific embodiment. As with the lateral spacers 21, each of the central spacers 22 and 23 can be provided in a number of sized, specifically with variations in the width between the lateral arms or legs of the spacers. Again, it is understood that the various dimensions of each of the spacer components of the device 20 is dictated by the particular anatomy of the vertebrae at the specific level, configured so that the device contacts the strongest bone of the vertebral body B.

Figure 20:
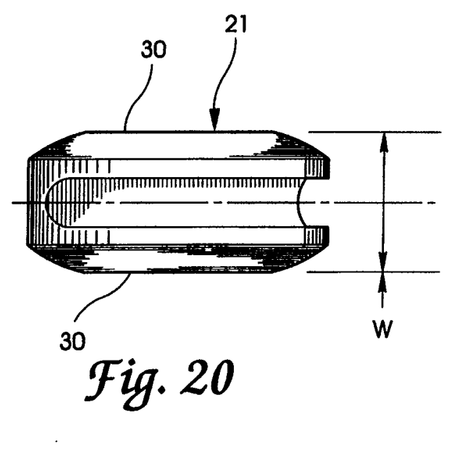
FIG. 20 is a side elevational view of the interbody fusion device shown in FIG. 6, illustrating the uniform thickness of the device.
Figure 21:
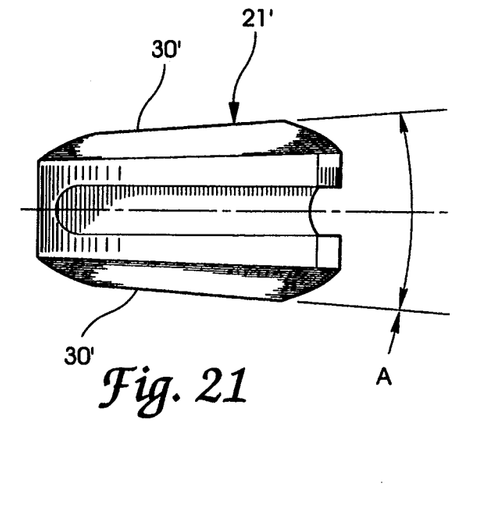
FIG. 21 is a side elevational view of an alternative configuration of an interbody fusion device similar to that shown in FIG. 20 with sagittal face angulation.

Moreover, the geometry of an appropriate fusion device can incorporate a fixed sagittal angle to maintain the patient's proper lordotic curvature once the device is implanted. As shown in FIG. 20, the device 21 has a fixed width W between end plate faces 30. Alternatively, a device 21' as shown in FIG. 21 can be provided in which the opposite end plate faces 30' diverge anteriorly at an angel A to approximate the sagittal angle, or lordosis, between two vertebrae.

It is expected that the bone graft material G housed within the interbody fusion device will fuse to the adjacent vertebrae. Bone cement or bone growth enhancing materials may be introduced with the graft material to enhance the initial and ultimate fusion of the vertebrae. In addition, it is anticipated, at least in one use of the present invention, that the disc annulus would be retained substantially intact, with the exception of an introduction portal in its anterior face. The disc annulus will exert a natural tension against the fusion device to provide stability to the disc space and to help maintain the device in its proper position for fusion.

Figure 22:
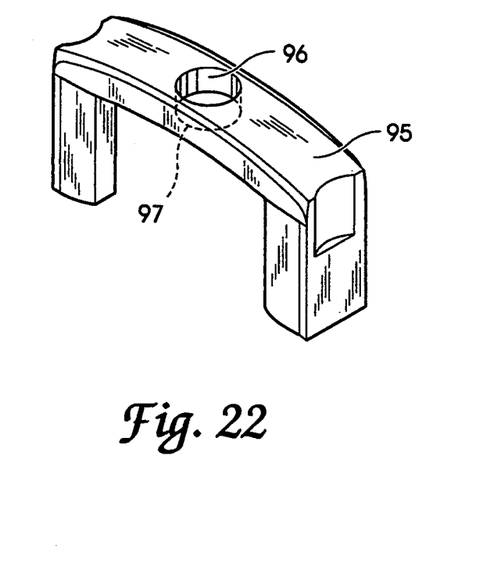
FIG. 22 is a bottom perspective view of an anterior spacer component modified from the component depicted in FIG. 11.
Figure 23:
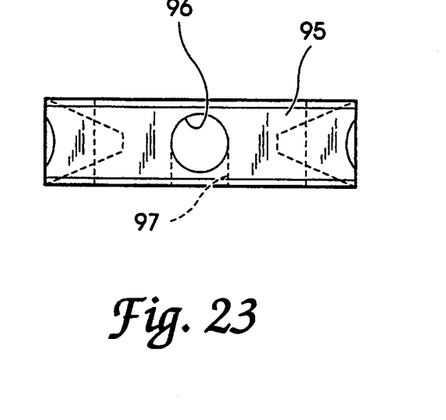
FIG. 23 is an end view of the anterior spacer component shown in FIG. 22.
Figure 24:
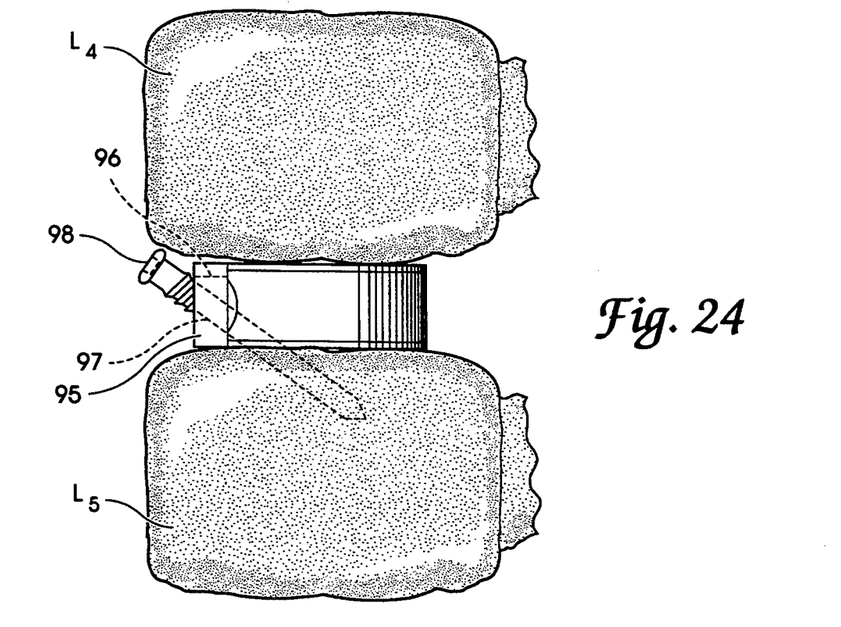
FIG. 24 is a view in the sagittal plane of an interbody fusion device arranged between two vertebrae in which the device includes the modified anterior spacer component depicted in FIGS. 22 and 23.

In some instances, greater initial fixation of the interbody fusion device to the vertebrae may be desirable. Greater fixation of the device can be accomplished using a modified anterior central spacer 95 shown in FIGS. 22 and 23. The spacer 95 is identical in most respects to the anterior spacer 22 described above. Like the prior spacer 22, the anterior spacer 95 includes a bore 96 extending through the front face of the spacer, which bore is aligned for use with a guide rod 85 for insertion of the spacer. However, the alternative anterior spacer 95 includes an angled bore 97 that intersects the guide bore 96 at an angle. This angled bore is configured to receive an anchoring bone screw 98 there through, which screw is ultimately threaded into a vertebra. FIG. 24 illustrates such a construct with the bone screw 98 partially threaded into the $L_5$ vertebra. The bone screw provides additional anchorage for the fusion device, which can speed the fusion process between the bone graft material G and the vertebrae.

Figure 25:
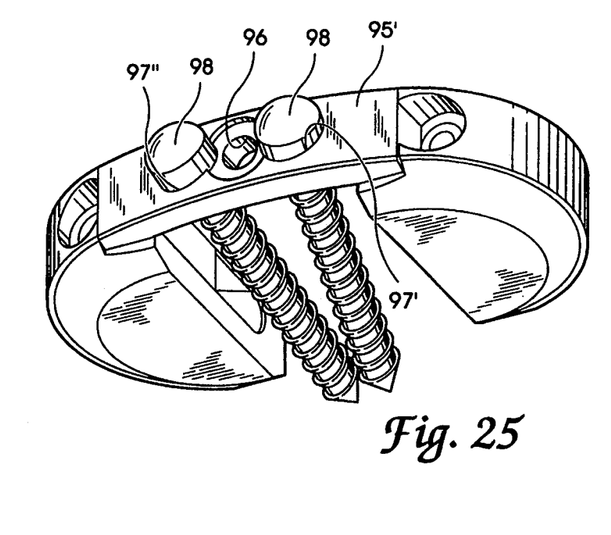
FIG. 25 is a bottom perspective view of an anterior interbody fusion device similar to the device depicted in FIG. 24, except using two anchoring screws.

Alternatively, two bone screws can be provided to anchor the device to one of the vertebrae. Such a device is illustrated in FIG. 25 showing an anterior spacer body 95' having a central guide bore 96 and two angled bores 97' and 97". The two angled bores 97' and 97" are configured to receive a corresponding bone screw 98 therethrough. The bores 97' and 97" are preferably (but not necessarily) oriented at different angles so that the two bone screws 98 can engage the vertebra without conflict.

The interbody fusion device of the previously described preferred embodiments utilizes two central spacers, such as posterior spacer 22 and anterior spacer 23 shown in FIG. 1. In an alternative embodiment, depicted in FIG. 26, only a single central spacer is utilized. Specifically, the interbody fusion device 120 of FIG. 26 includes a pair of lateral spacers 21 as previously described. However, instead of a posterior and an anterior central spacer, the device 120 includes a single midline central spacer 122 formed by a body 123 spanning between the lateral spacers and by elongated dovetail arms 124 formed at the opposite ends of the body 123. Each of the dovetail arms 124 is configured to be slidably received within the interlock channels 34 of the lateral spacers. Each of the arms 124 includes a posterior portion 125, configured to contact the end walls 35 (FIG. 6) of the lateral spacers. The arms further include an anterior portion 126 against which the fixation screws 24 act to hold the assembly together.

Figure 26:
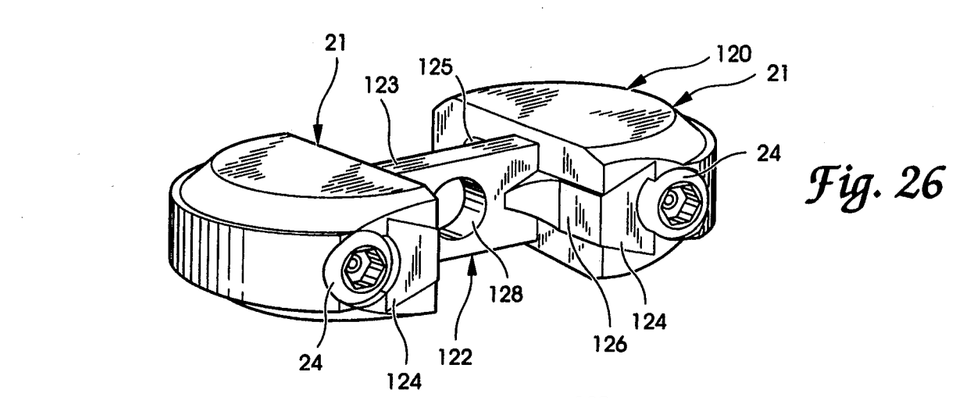
FIG. 26 is a front perspective view of an alternative embodiment of an anterior interbody fusion device according to the present invention utilizing a single central spacer.

The body 123 of the midline central spacer 122 includes a guide bore 128 defined therethrough which is used as described above to guide the in situ insertion of the spacer 122 between the two lateral spacers 21. The fusion device 120 is thus assembled in a manner similar to the previous device 20, except that only one central spacer is inserted. Bone graft material is preferably placed between the separated lateral spacers 21 prior to and after insertion of the midline central spacer 122, to completely fill the cavity defined by the interbody fusion device 120. Alternatively, the central spacer 122 can be configured so that the body 123 is situated at the anterior or posterior face of the lateral spacers 21, as shown in FIG. 25, for example. When configured in this manner, the arms 124 of the spacer would not include anterior and posterior portions 125 and 126, but would include but a single extension that would traverse the entire length of the interlocking channel 34 from the anterior face to the end wall 35.

Figure 27:
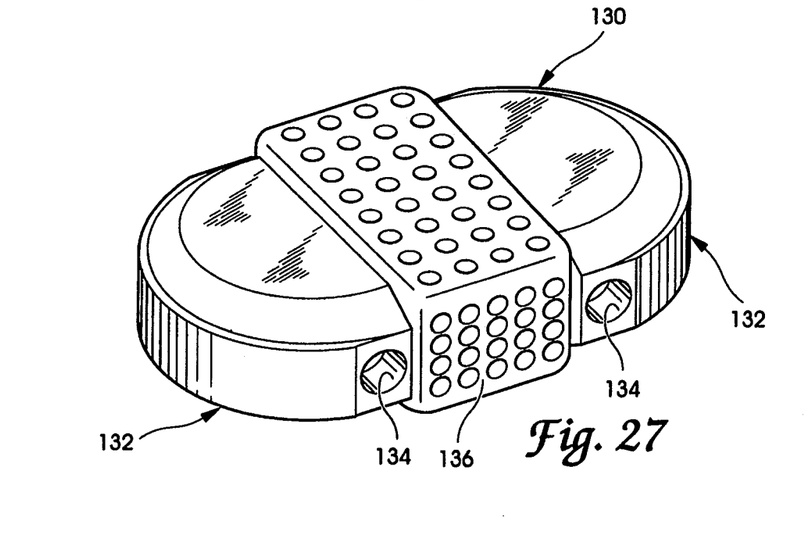
FIG. 27 is a top perspective view of a further embodiment of the invention in which a bone graft material insert is shaped for disposition between two lateral spacers of the device.

In yet another embodiment of the invention, a fusion device 130 includes a pair of modified lateral spacers 132. These lateral spacers do not include the dovetail interlocking channel 34 of the prior described spacers. The spacers 132 are, however, provided with guide bores 134 in their anterior face to receiving an insertion rod 80 (FIG. 14) used to insert and spread the lateral spacers 132 within the intradiscal space. The fusion device 130 includes a bone graft insert 136 shaped to be received within the intradiscal space between the separated lateral spacers 132. The device 130 is maintained in its assembled configuration by the natural tension of the disc annulus surrounding the components. Alternatively, the bone graft insert 136 can be shaped to include dovetail arms, in the manner of the central spacers 22 and 23, for engagement with interlocking channels 34 of lateral spacers 21.

Figure 28:
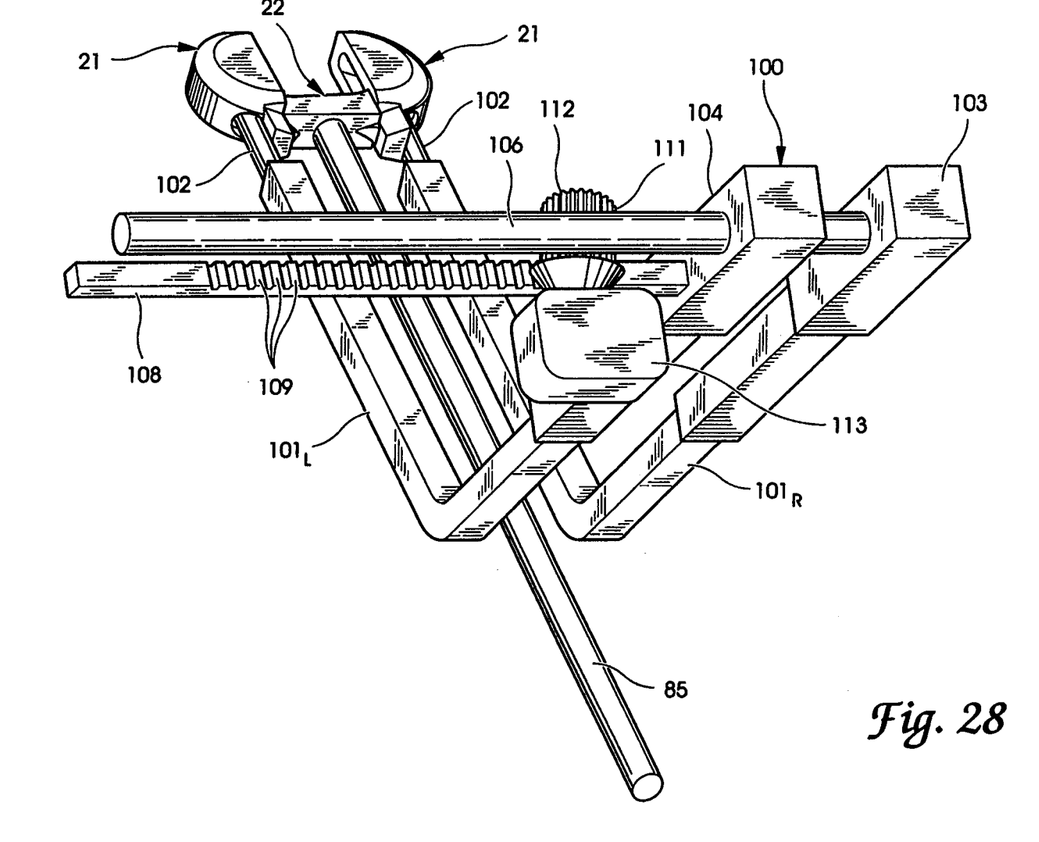
FIG. 28 is a top perspective view of instrumentation for insertion of the interbody fusion device of the present invention.

Insertion instrumentation has been previously described to accomplish the piecemeal construction of the assembled interbody fusion device through a minimally invasive portal. A further embodiment of insertion instrumentation is illustrated in FIG. 28, and more particularly a spreader assembly 100. The spreader assembly 100 provides a means for spreading the lateral spacers 21 apart within the disc space and to that extent is intended as a substitute for manually manipulated spreader rods 80 previously described, while still locating off of similar spreader rods.

Specifically, the spreader assembly 100 includes a pair of spreader bars 101 which engage at their ends with spreader rod portions 102. The spreader rod portions 102 are configured similar to the end of the rods 80 for reception within the screw bores 37 of the lateral spacers 21. Two spreader bars, $101_R$ and $101_L$ are provided, each of which are bent at an obtuse angle distal from the spreader rod portions 102. The opposite end of each of the bent bars $101_R$ and $101_L$ is mounted to a respective guide body 103 or 104.

Mounted to and projecting from the left guide body 104 is a guide rod 106, and mounted to the right guide body is an advancement rack 108. The advancement rack 108 extends through a rectangular bore defined in the left guide body 104 so that the guide body 104 can slide over the rack. The guide rod 106 terminates without engaging the right guide body 103 to acts as a stop or limit to the relative movement of the left guide body 104 toward the right body 103. The advancement rack 108 includes a number of teeth 109, configured in the form of a rack and pinion system, to engage teeth 112 of a pinion gear 111. A knob 113 is provided for rotating the pinion gear 111 to advance the rack 108 relative to the guide rod 106. As the rack 108 moves relative to the rod 106, it pushes the right guide body 103 (to which the rack is connected) away from the left guide body 104 (to which the rod is connected).

In the illustrated embodiment, the pinion gear 111 includes teeth 112 around the entire circumference of the gear, which means that some of the teeth will contact the toothless surface of the guide rod 106. Alternatively, the pinion gear 111 can include teeth around only a portion of the gear's circumference. Since the lateral spacers 21 need only be separated enough to permit introduction of the two central spacers, the relative travel between the two spreader bars $101_R$ and $101_L$, and likewise the guide bodies 103 and 104, is limited. As a consequence, the amount of travel of the rack 108 and the corresponding rotation of the pinion gear 111 are also limited. In the preferred embodiment, about one-half rotation of the pinion gear 111 accomplishes the necessary separation of the two lateral spacers 21, so that the teeth 112 need only extend about half way around the gear.

Once the rack and pinion have been properly manipulated to separate the two lateral spacers 21, the posterior central spacer 22 can be introduced by way of the guide rod 85. The bend in the two spreader bars 101 provided clearance to manipulate the central spacer 22 and rod 85 between the bars. The anterior central spacer 23 can be assembled in a similar mariner, after which the spreader assembly 100 is removed from the surgical site.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An interbody fusion device configured for introduction into an intradiscal space defined by a disc annulus between two adjacent vertebrae, the intradiscal space defining a predetermined area relative to the adjacent vertebrae, the interbody fusion device comprising:

a pair of lateral spacers, each having opposite endplate faces adapted to contact each of the adjacent vertebrae when said lateral spacers are within the intradiscal space, and each having a side face defining a channel therein; and a first central spacer having opposite faces oriented toward each of the adjacent vertebrae when said first central spacer is within the intradiscal space, and further having opposite ends, each of said opposite ends configured to be slidably received within said channel in a corresponding one of said lateral spacers, wherein said pair of lateral spacers and said first central spacer are sized for individual introduction into the intradiscal space for assembly within the intradiscal space with said opposite ends of said first central spacer engaged within said channel in said corresponding one of said lateral spacers.

2. The interbody fusion device of claim 1, wherein said endplate faces of each of said pair of lateral spacers and said opposite faces of said first central spacer each define an area that is substantially less than the area of the intradiscal space.

3. The interbody fusion device of claim 1, wherein said first central spacer is elongated with a length between said opposite ends, said length being sized such that said lateral spacers are adjacent the disc annulus when said first central spacer is assembled with each of said pair of lateral spacers.

4. The interbody fusion device of claim 1, further comprising:
an elongated second central spacer having second opposite faces oriented toward each of the adjacent vertebrae and second opposite ends configured to be slidably received within said channel in a corresponding one of said lateral spacers, and
wherein when said second central spacer is assembled with said lateral spacers and said first central spacer within the intradiscal space a cavity is defined by said side face of each of said lateral spacers and said first and second central spacers, said cavity sized for introduction of bone graft material therein.

5. The interbody fusion device of claim 4, wherein:
said channel in each of said lateral spacers has a channel length;
said first central spacer has a first pair of arms defined at each of said opposite ends, said first pair of arms configured to be slidably received within said channel in a corresponding one of said lateral spacers to extend along a first portion of said channel length;
said second central spacer has a second pair of arms defined at each of said second opposite ends, said second pair of arms configured to be slidably received within said channel in a corresponding one of said lateral spacers to extend along a remaining portion of said channel length; and
each of said first pair of arms contacts a corresponding one of said second pair of arms within said channel in a corresponding one of said lateral spacers to maintain a predetermined spacing between said first and second central spacers thereby defining said cavity.

6. The interbody fusion device of claim 5, wherein:
said channel in each of said lateral spacers has an end wall at one end of said channel length and an opening at an opposite end of said channel length for introduction of the corresponding first and second arms of said first and second central spacers; and
said device further includes clamping means at said opposite end of said channel length for clamping said corresponding first and second arms within a corresponding channel, said clamping means bearing against said second central spacer to clamp said second pair of arms against said first pair of arms and said first pair of arms against said end wall of said corresponding channel.

7. The interbody fusion device of claim 6, wherein:
each of said lateral spacers defines a threaded bore adjacent said channel; and
said clamping means includes a threaded fastener having an enlarged head at one end for engaging said first central spacer when said fastener is threaded into said bore.

8. The interbody fusion device of claim 5, wherein:
said channel in each of said lateral spacers and each of said first and second pair of arms are configured for interlocking engagement to prevent removal of the corresponding axis from the corresponding channels in any direction other than along said channel length.

9. The interbody fusion device of claim 8, wherein said channel in each of said lateral spacers is a dovetail channel and each of said first and second pair of arms is configured as a dovetail.

10. The interbody fusion device of claim 1, wherein:
said channel in each of said lateral spacers has a channel length; and
said first central spacer includes an elongated arm at each of said opposite ends, each of said arms being configured to be slidably received within said channel and each having a length substantially equal to said channel length.

11. The interbody fusion device of claim 10, wherein said elongated arm at each of said opposite ends of said first central spacer includes a posterior portion disposed between said central spacer and one end of said channel and an anterior portion disposed between said central spacer and the opposite end of said channel.

12. The interbody fusion device of claim 10, wherein:
said channel in each of said lateral spacers has an end wall at one end of said channel length and an opening at an opposite end of said channel length for introduction of the corresponding arm at said opposite ends of said first central spacer; and
said device further includes clamping means at said opposite end of said channel length and bearing against said first central spacer for clamping said corresponding arm against said end wall of said corresponding channel.

13. The interbody fusion device of claim 12, wherein:
each of said lateral spacers defines a threaded bore adjacent said channel; and
said clamping means includes a threaded fastener having an enlarged head at one end for engaging said first central spacer when said fastener is threaded into said bore.

14. The interbody fusion device of claim 10, wherein:
said channel in each of said lateral spacers and said arm at said opposite ends of said first central spacer are configured for interlocking engagement to prevent removal of the corresponding arms from the corresponding channels in any direction other than along said channel length.

15. The interbody fusion device of claim 14, wherein said channel in each of said lateral spacers is a dovetail channel and said arm at each of said opposite ends of said first central spacer is configured as a dovetail.

16. A device for introducing an interbody fusion device into an intradiscal space defined by a disc annulus between two adjacent vertebrae, in which the interbody fusion device includes a pair of lateral spacers adapted to contact each of the adjacent vertebrae and a central spacer for mating engagement with the central spacers within the intradiscal space, each of the pair of lateral spacers and central spacer sized for individual introduction into the intradiscal space for assembly therein, said device comprising:

a pair of spreader rods, one for each of said pair of lateral spacers, each having means for engaging a respective one of said lateral spacers, and each sized to extend outside the patient when engaging said lateral spacers disposed within the intradiscal space; and means for manipulating said pair of spreader rods outside the patient to move said lateral spacers apart within the intradiscal space.

17. The device of claim 16, wherein said means for manipulating includes a rack and pinion gear assembly engaged between said pair of spreader bars so that rotation of said pinion gear along said rack causes said pair of spreader bars to move apart.

18. The interbody fusion device of claim 1, wherein:

said first central spacer defines a bore therethrough, said bore having an axis angled toward an adjacent vertebra when said first central spacer is disposed within the intradiscal space; and said device further comprises a bone screw sized for introduction through said bore in said central spacer to engage the adjacent vertebra and thereby anchor said first central spacer to the vertebra.

* * * * *